(12) United States Patent
Gemmel et al.

(10) Patent No.: US 11,382,592 B2
(45) Date of Patent: Jul. 12, 2022

(54) INCREASING ACCURACY OF POSITIONING A MOBILE MEDICAL X-RAY DEVICE RELATIVE TO AN EXAMINATION SUBJECT USING A CAMERA SYSTEM

(71) Applicant: Siemens Healthcare GmbH, Erlangen (DE)

(72) Inventors: Alexander Gemmel, Erlangen (DE); Gerhard Kleinszig, Forchheim (DE); Bjoern Kreher, Bräuningshof (DE); Holger Kunze, Bubenreuth (DE); Jessica Magaraggia, Erlangen (DE); Markus Weiten, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 286 days.

(21) Appl. No.: 16/833,412

(22) Filed: Mar. 27, 2020

(65) Prior Publication Data
US 2020/0305832 A1    Oct. 1, 2020

(30) Foreign Application Priority Data
Mar. 28, 2019   (DE) .................. 102019204361.5

(51) Int. Cl.
*A61B 6/00*  (2006.01)
*A61B 6/02*  (2006.01)
*A61B 6/04*  (2006.01)

(52) U.S. Cl.
CPC ............. *A61B 6/547* (2013.01); *A61B 6/022* (2013.01); *A61B 6/0487* (2020.08);
(Continued)

(58) Field of Classification Search
CPC .............................. A61B 6/547; A61B 6/0487
See application file for complete search history.

(56) References Cited

U.S. PATENT DOCUMENTS

2015/0327824 A1* 11/2015 Kleinszig ................ G06T 7/38
                                                            378/62
2016/0296185 A1   10/2016 Gemmel
(Continued)

FOREIGN PATENT DOCUMENTS

DE    102013221383 A1    4/2015
DE    102015205096 A1    11/2015
(Continued)

OTHER PUBLICATIONS

German Office Action for German Application No. 10 2019 204 361.5 dated Jan. 24, 2020.

*Primary Examiner* — Dani Fox
(74) *Attorney, Agent, or Firm* — Lempia Summerfield Katz LLC

(57) ABSTRACT

A method for increasing accuracy of positioning an X-ray device relative to an examination subject using a camera system includes recording a first data set, acquiring original positioning information pertaining to the X-ray device and specifying a target position of the X-ray device relative to the original position. The X-ray device is positioned out of the original position into a first approach position using the original positioning information, and a second data set is recorded. A deviation between the target position and the first approach position is determined by a reconciliation between the first data set and the second data set. The X-ray device is positioned out of the first approach position into a second approach position using the determined deviation.

21 Claims, 6 Drawing Sheets

(52) U.S. Cl.
CPC .......... *A61B 6/4208* (2013.01); *A61B 6/4405* (2013.01); *A61B 6/4441* (2013.01); *A61B 6/461* (2013.01)

(56) References Cited

U.S. PATENT DOCUMENTS

2017/0052670 A1    2/2017   Gemmel
2019/0069864 A1    3/2019   Tkaczyk

FOREIGN PATENT DOCUMENTS

| DE | 102015206158 A1 | 10/2016 |
| DE | 102015215820 A1 | 2/2017 |
| DE | 102016213050 A1 | 1/2018 |

* cited by examiner

INCREASING ACCURACY OF POSITIONING A MOBILE MEDICAL X-RAY DEVICE RELATIVE TO AN EXAMINATION SUBJECT USING A CAMERA SYSTEM

This application claims the benefit of German Patent Application No. DE 10 2019 204 361.5, filed Mar. 28, 2019, which is hereby incorporated by reference in its entirety.

BACKGROUND

The present embodiments relate to increasing accuracy of positioning of a mobile medical X-ray device relative to an examination subject using a camera system.

It is known from the prior art that, in pre- or intraoperative imaging methods using a mobile medical X-ray device, positioning of the X-ray device often occurs. These methods are known, for example, as "Park-and-Return" or "Panoramic Imaging" and allow a targeted return or movement of the X-ray device to the original recording position or to a target position. The known methods for the positioning of a mobile X-ray device are often based on data relating to a position determination by a movement apparatus of the X-ray device. The disadvantage here is that this position determination data is prone to error due to external influences on the movement apparatus during the positioning (e.g., slippage) as a function of the movement distance that has been covered. Further known methods, with a movement of the X-ray device by a robotic arm, for example, are likewise prone to error due to a deviation in the position determination of a pose of the robotic arm.

Further known solutions for the positioning of a mobile X-ray device use an external system, such as a laser scanner or an external tracking system. The disadvantage is the cost outlay and the additional modification measures required. This is difficult to implement (e.g., in a surgical environment).

SUMMARY AND DESCRIPTION

The scope of the present invention is defined solely by the appended claims and is not affected to any degree by the statements within this summary.

The present embodiments may obviate one or more of the drawbacks or limitations in the related art. For example, an accuracy when positioning a mobile medical X-ray device relative to an examination subject using a camera system is increased.

The medical X-ray device includes a detector. The camera system has a defined position relative to the detector. A first data set that maps at least one first section of a surface structure of the examination subject is recorded at a first point in time by the camera system. Original positioning information relating to the X-ray device at the first point in time is acquired. The X-ray device is in an original position at the first point in time. In addition, a target position of the X-ray device relative to the original position is specified. The original position is described by the original positioning information and the first data set. Next, the X-ray device is positioned out of the original position into a first approach position by the original positioning information. A further data set that maps at least one further section of the surface structure of the examination subject is recorded at a further point in time by the camera system. At a further point in time, the X-ray device is located in the first approach position. The at least one first section and the at least one further section at least partly map a common region of the surface structure of the examination subject. Through a reconciliation between the first data set and the further data set, a deviation between the target position and the first approach position is determined. The X-ray device is positioned out of the first approach position into a second approach position using the deviation that has been determined.

For example, when recording the further data set, a plurality of further data sets that map at least one further section of the surface structure of the examination subject may be recorded at the further point in time by the camera system.

For example, the surface structure may include texture-related information and/or depth-related information and/or material-related information. The data set that maps a section of the surface structure of the examination subject may include a plurality of, for example, different, partial information items (e.g., texture-related information and/or depth-related information and/or reflection-related information and/or absorption-related information). This data set, which maps a section of the surface structure of the examination subject, may be recorded by the camera system. Through the defined position of the camera system relative to the detector, the data set may enable a three-dimensional reconstruction of the section of the surface structure of the examination subject that has been mapped. Through the three-dimensional reconstruction, an accurate (e.g., true-to-scale) reproduction in the data set of the section of the surface structure of the examination subject that is mapped is facilitated.

In an exemplary embodiment, the camera system may include one or a plurality of recording units (e.g., cameras). The camera system may include, for example, a depth camera and/or a laser scanner system and/or an infrared camera and/or a stereo camera system. The camera system may be embodied to record the surface structure of an examination subject in a data set. One or a plurality of recording units that each record at least one partial information item relating to the surface structure may be combined in a camera system. Further sensors, such as distance sensors and/or ultrasound sensors, may be combined advantageously with the camera system.

For example, the camera system has a defined position relative to the detector. The camera system may be arranged on a mounting of the X-ray device. As a result of this, the camera system may be directly connected to the X-ray device and also be moved with the X-ray device to the same extent. For example, the position of the camera system relative to the X-ray device may be changed or halted by the mounting; the position of the camera system relative to the detector is accurately defined. This may allow a change in the direction of view of the camera system onto the examination subject (e.g., before recording the first data set). In one embodiment, in a camera system that includes a plurality of recording units, the position of the individual recording units relative to one another may be changed. A data set that maps one section of the surface structure of the examination subject may be registered onto a changed arrangement of the recording units of the camera system. In an embodiment, the camera system may include an additional recording unit that is provided separately (e.g., in a fixed location, at a defined position relative to the detector in the room, and/or on the X-ray device).

The original positioning information pertaining to the X-ray device includes the original position of the X-ray device in the room and/or relative to a point of reference (e.g., a parking position in the room). The original positioning information may include information about the alignment of the detector and/or of further components of the X-ray device and/or of a pose of the X-ray device (e.g., in the case of a robotic arm). The original position is the spatial position and/or position of the X-ray device at the first point in time. For example, the original positioning information may be determined separately from information on the alignment of the detector and/or of further components of the X-ray device and/or of a pose of the X-ray device, for example, by an input from an operator (e.g., of a target position in the case of a previous movement of the X-ray device to the original position).

The positioning of the X-ray device out of the original position into a first approach position using the original positioning information may include a movement and/or an alignment of the X-ray device. A direction and a distance starting from the original positioning may be specified as a target position. The first approach position may then be determined by the original positioning information and information about the specified target position relative to the original position.

The first approach position may include at least one part of the original positioning information, for example, as the origin of a system of coordinates for determining the target position. Using the original positioning information, the original position of the X-ray device in the room and/or relative to a reference point in the room may be determined. Using the original positioning information and the first data set, the target position of the X-ray device in the room and/or relative to the original position may be specified.

The at least one further section of the surface structure at least partly maps a common region of the surface structure of the examination subject as does the first section of the surface structure. The further section of the surface structure is mapped by the further data set, which is recorded at a further point in time by the camera system. At the further point in time in the recording of the further data set, the X-ray device is in the first approach position.

The positioning of the X-ray device out of the original position into the first approach position has an accuracy that facilitates an at least partly common imaging region of the surface structure of the examination subject through the camera system.

A deviation between the target position and the first approach position can ensue through a reconciliation of the first data set and the further data set. Here, in particular, a reconciliation of a plurality of features that are encompassed by the first and by the further data set, such as texture-related information and/or depth-related information and/or reflection-related information and/or absorption-related information, can be advantageous. In particular, the deviation between the target position and the first approach position can in turn include texture-related information and/or depth-related information and/or reflection-related information and/or absorption-related information.

The accuracy of the positioning of the X-ray device may be increased through a positioning downstream (e.g., chronologically) out of the first approach position into a second approach position by the deviation that has been determined. For example, through the positioning being downstream (e.g., chronologically), a deviation between the first approach position and the target position may be reduced.

In a further embodiment, the X-ray device is moved to an intermediate position before the positioning into the first approach position. The original position may be specified as the target position. This embodiment may facilitate, for example, the return of the X-ray device to the original position after positioning in an intermediate position (e.g., in the case of "Park-and-Return"). In the reconciliation between the first data set and the further data set, a deviation between the original position and the first approach position is determined.

Using the original positioning information and the specification of the target position, the X-ray device may be moved out of the intermediate position up to the first approach position. Next, the positioning of the X-ray device out of the first approach position into the second approach position may ensue using the first data set and the further data set. Since long distances are often covered in the positioning of the X-ray device into the intermediate position and the return of the X-ray device to the original position, this embodiment is advantageous for reducing error in the positioning of the X-ray device.

The intermediate position may include, for example, a parking position of the X-ray device into which the X-ray device is moved out of the original position after the first point in time. The intermediate position may be the spatial position and/or location of the X-ray device at a point in time after the first point in time. The intermediate position may also be formed, for example, by an intermediate pose of the X-ray device (e.g., in the case of a robotic arm). This is advantageous, for example, in order to allow unimpeded access to the examination subject.

For example, the positioning of the X-ray device may ensue on a different motion pathway than the change in the position of the X-ray device after the first point in time out of the original position into the intermediate position. This may be advantageous, for example, for collision-free positioning.

In an embodiment, a graphic representation of a section of the surface structure of the examination subject (e.g., recorded currently) may be displayed on a monitor and/or a display, for example. This may be advantageous, for example, in the case of a manual or semi-automatic positioning of the X-ray device by an operator since a change in the section recorded by the camera system may be observed directly in the graphic representation of the surface structure that is displayed.

In a further embodiment, a deviation between the first data set and the further data set is determined. A representation of the deviation is displayed on a display unit (e.g., a monitor for and/or a display). For example, the deviation may include a numerical value and/or image information. The representation of the deviation on a display unit is advantageous, for example, for direct feedback on the accuracy of the positioning of the X-ray device out of the original position into the first approach position and/or on changes inside the recording region of the camera system (e.g., changes in the examination subject).

In a further embodiment, a graphic representation of a transformation that merges the further (e.g., last recorded) data set into the first data set may be displayed on the display unit.

In a further embodiment, at a time during the positioning of the X-ray device out of the first approach position into the second approach position, a correction of this positioning of the X-ray device ensues. This correction includes a recording of at least one further current data set and a reconciliation of this further current data set with at least one data set recorded earlier.

For example, in a surgical environment, it may happen that at least one sub-region of a field of view of the camera system is obscured by an apparatus and/or by an operator. By recording the at least one further current data set during the positioning out of the first approach position into the second approach position, a correction of the positioning may ensue. If, for example, a previously obscured sub-region of the field of view of the camera system becomes free, then by recording the further current data set and the subsequent reconciliation with the at least one data set recorded earlier, an improved positioning may ensue. Through the recording of the further current data set and the reconciliation with the at least one data set recorded earlier, a change in the examination subject and/or a change in the location of the examination subject during the positioning out of the first approach position into the second approach position may be detected and corrected.

In a further embodiment, the positioning of the X-ray device out of the first approach position into the second approach position may ensue semi-automatically or automatically. Through the automation of the positioning of the X-ray device, a, for example, guided alignment of the movement of the X-ray device during the positioning may ensue. As a result, an input regarding a movement of the X-ray device by the operator, for example, for a determination of the speed of movement may be simplified. For example, the movement apparatus may have a motorized drive, by which at least one motorized movement support of the X-ray device may ensue. With automatic positioning of the X-ray device, a motorized movement of the X-ray device may ensue at least in individual sections of the movement (e.g., between the original position and an intermediate position and/or during the positioning out of the intermediate position into the first approach position and/or during the positioning out of the first approach position into the second approach position). For example, through a semi-automatic or automatic positioning, a navigation may ensue (e.g., an alignment of the movement of the X-ray device during the positioning and/or the positioning). The navigation may facilitate a collision-free movement within the degrees of freedom of movement of the X-ray device.

In a further embodiment, a parameter for the registrability between the, for example, last recorded further data set and the first data set may be acquired. The parameter is displayed on a display unit. The registrability may be characterized, for example, by a capability for registration of the, for example, last recorded, further data set and the first data set. For example, the parameter for registrability may be determined by what proportion the section of the surface structure of the examination subject that is mapped by the first data set is contained in the section of the surface structure that is mapped by the further data set (e.g., a second data set). Through the display of the parameter for the registrability on a display unit (e.g., on an LED display and/or on a display), direct feedback may be given to the operator regarding the reliability of the positioning.

In a further embodiment, a graphic pattern may be projected onto the surface of the examination subject that may be tracked by the camera system. As a result, a graphic pattern that is, for example, visible and/or not visible may be projected onto the surface of the examination subject. As a result of this, the recording of a data set that maps the surface structure of the examination subject by a single camera, for example, is facilitated. Through the projection of a graphic pattern onto the surface of the examination subject, an improvement of the mapping of the surface structure in the recorded data set may be achieved.

In a further embodiment, the camera system includes at least two cameras. The at least two cameras each record at least one data subset that maps at least one common section of the surface of the examination subject. The first data set and the further data set each include at least one data subset from each of the at least two cameras. Each data subset may map a section of the surface of the examination subject. A section of the surface structure of the examination subject may be mapped by combining the data subsets. Due to the redundancy of recording devices within the camera system, positioning of the X-ray device from the first approach position into the second approach position may even ensue when the field of view of one of the recording devices is obscured.

In a further embodiment, patient-positioning information may be assigned to the original positioning information, where registration of the first data set onto a change in the patient-positioning information ensues at the time of recording the further data set. As a result, positioning of the X-ray device out of the first approach position may ensue even when the patient-positioning information has changed (e.g., when there is a change in the location of the section of the surface structure that may be detected by the camera system as a result thereof). It is possible to respond to a change in patient-positioning information (e.g., operation-related) by registration of the first data set.

In a further embodiment, texture-related information may be assigned to each recorded data set. For example, by assigning texture-related information, a distinction may be facilitated between different materials and/or types of tissue on the surface structure of the examination subject. This may be advantageous for distinguishing anatomical regions of the examination subject from, for example, surgical instruments and/or a patient positioning unit and/or surgical drapes. As a result, the accuracy of the positioning out of the first approach position into the second approach position may be increased.

In a further embodiment, the mobile X-ray device includes a movement apparatus, where the original positioning information in the X-ray device is captured via changes inside the movement apparatus and/or relative to a mounting on the movement apparatus. As a result, it is possible, for example, to dispense with additional components and/or modification measures for acquiring the original positioning information pertaining to the X-ray device. For example, the movement apparatus of the X-ray device may include a mounting. The mounting may include, for example, a rail system and/or a base for a robotic arm. The original positioning information may be determined via changes relative to the mounting of the movement apparatus.

In an embodiment, the original positioning information for the X-ray device may be at least partly determined by an X-ray device acquisition unit. The X-ray device acquisition unit may include, for example, a camera system and/or a motion sensor and/or a laser scanner system. For example, as a result, the original positioning information may be acquired with respect to a reference point in the room (e.g., the intermediate position) By incorporating positioning information from the X-ray device acquisition unit, absolute position-related information may be assigned to the original positioning information in addition to the relative positioning information in the X-ray device and/or the positioning information in the X-ray device. As a result, for example, collision-free positioning of the X-ray device out of the original position into the first approach position may be facilitated.

In a further embodiment, the movement apparatus includes at least one wheel. The original positioning information in the X-ray device is at least partly determined via wheel setting changes. Via the wheel setting changes, both a movement direction of the X-ray device and/or alignment information and/or relative position-related information may be assigned to the original position-related information. As a result, a determination of the original positioning information may be incorporated directly into the movement apparatus and without the need for additional components and/or modification measures. The wheel setting changes may be determined, for example, via optical and/or electrical and/or mechanical sensors. In a further embodiment, the at least one wheel may be embodied as a sensor in the movement apparatus. The original positioning information may be at least partly determined by one encoder or a plurality of encoders.

A medical X-ray device that is embodied to carry out one or more of the proposed methods is provided. For example, the X-ray device includes a detector and a camera system that is embodied to record a data set that maps at least one first section of the surface structure of the examination subject. The camera system has a defined position relative to the detector. Through the defined position of the camera system relative to the detector of the X-ray device, a precise assignment of the position and/or of the location of each data set that has been recorded by the camera system is facilitated. Through the defined (e.g., fixed) position of the camera system relative to the detector, it is possible to provide that the camera system is moved to the same extent as the detector during a movement (e.g., a re-alignment and/or positioning) of the X-ray device.

A medical X-ray device that is embodied to carry out another embodiment of the proposed method is provided. The X-ray device includes a detector and a camera system that is embodied to record a data set that maps at least one first section of the surface structure of the examination subject. The camera system has a defined position relative to the detector. The X-ray device includes a display unit (e.g., a display and/or an LED display and/or a monitor).

In one embodiment, the X-ray device includes a detector and a camera system that is embodied to record a data set that maps at least one first section of a surface structure of the examination subject. The camera system has a defined position relative to the detector, and the X-ray device includes a projection device that is embodied to project a graphic pattern onto the surface of the examination subject that may be mapped by the camera system. A graphic pattern that is, for example, visible and/or not visible (e.g., a grid network and/or a geometrical scatter plot) may be projected onto the surface of the examination subject. As a result, for example, the recording of a data set that maps the surface structure of the examination subject using, for example, a single camera may be facilitated, even in poor lighting conditions, such as, for example, darkness. By detecting a distortion of the geometric pattern in the data set that has been recorded, the surface structure of the examination subject may be mapped.

In one embodiment, the X-ray device includes a detector and a camera system that is embodied to record a data set that maps at least one first section of a surface structure of the examination subject. The camera system has a defined position relative to the detector, and the camera system includes at least two cameras. The at least two cameras are each embodied to record at least one data subset that maps at least one common section of a surface of the examination subject. The data subsets include stereoscopic information. The stereoscopic information maps at least one section of the surface structure of the examination subject. The first data set and the further data set each include at least one data subset from each of the at least two cameras.

In one embodiment, the X-ray device includes a detector and a camera system that is embodied to record a data set that maps at least one first section of a surface structure of the examination subject. The camera system has a defined position relative to the detector. The X-ray device includes a movement apparatus. The original positioning information in the X-ray device may be acquired via changes inside the movement apparatus and/or relative to a mounting of the movement apparatus.

In one embodiment, the X-ray device includes a detector and a camera system that is embodied to record a data set that maps at least one first section of a surface structure of the examination subject. The camera system has a defined position relative to the detector, and the X-ray device includes a movement apparatus that includes at least one wheel. The original positioning information of the X-ray device may be at least partly acquired via wheel setting changes.

The medical X-ray device may include a display unit (e.g., a display and/or a monitor and/or an LED display) that is embodied to display information and/or graphic representations of information in the X-ray device and/or the camera system, and/or of further components.

The advantages of the X-ray device of the present embodiments essentially correspond with the advantages of the method of the present embodiments for increasing the accuracy of positioning of a mobile medical X-ray device relative to an examination subject using a camera system. Features, advantages, or alternative embodiments mentioned herein may equally well be applied to the other subject matter and vice versa.

A computer program product is also provided (e.g., stored on a non-transitory computer-readable storage medium). The computer program product includes a computer program (e.g., including instructions) and may be loaded directly into a memory unit of a programmable computation unit, and programming means, such as libraries and auxiliary functions, in order to carry out a method for increasing the accuracy of positioning of a mobile medical X-ray device relative to an examination subject using a camera system when the computer program (e.g., including instructions) is run. The computer program product may include software with a source code that still has to be compiled and bound or merely interpreted, or include an executable software code that only has to be loaded into the processor for execution. Using the computer program product, the method for increasing the accuracy of positioning of a mobile medical X-ray device relative to an examination subject using a camera system may be carried out quickly in an identically reproducible manner and robustly. The computer program product is configured such that the computer program product may carry out the process acts according to the present embodiments using the processor. The processor may in each case have the prerequisites for an appropriate main memory, an appropriate graphics card, or an appropriate logic unit, such that the respective process acts may be carried out efficiently.

The computer program product is stored, for example, on a computer-readable medium (e.g., a non-transitory computer-readable storage medium), or on a network or server from which the computer program product may be loaded into the processor of a computer. The processor is directly connected to the computer or may be embodied as part of the computer. Control data relating to the computer program product may be stored on an electronically readable data carrier (e.g., non-transitory). The control data in the electronically readable data carrier may be embodied such that the control data carries out a method according to the present embodiments when the data carrier is used in a processor. Examples of electronically readable data carriers are a DVD, a magnetic tape, or a USB stick, on which electronically readable control data (e.g., software) is stored. When this control data is read by the data carrier and stored in a processor, all the embodiments of the method described in the aforementioned may be carried out. The present embodiments may therefore also take as a point of departure the computer-readable medium and/or the electronically readable data carrier.

BRIEF DESCRIPTION OF THE DRAWINGS

Exemplary embodiments of the invention are shown in the drawings and are described in greater detail hereinafter. In different figures, the same reference signs denote same features. The figures show.

DETAILED DESCRIPTION

Figure 1:
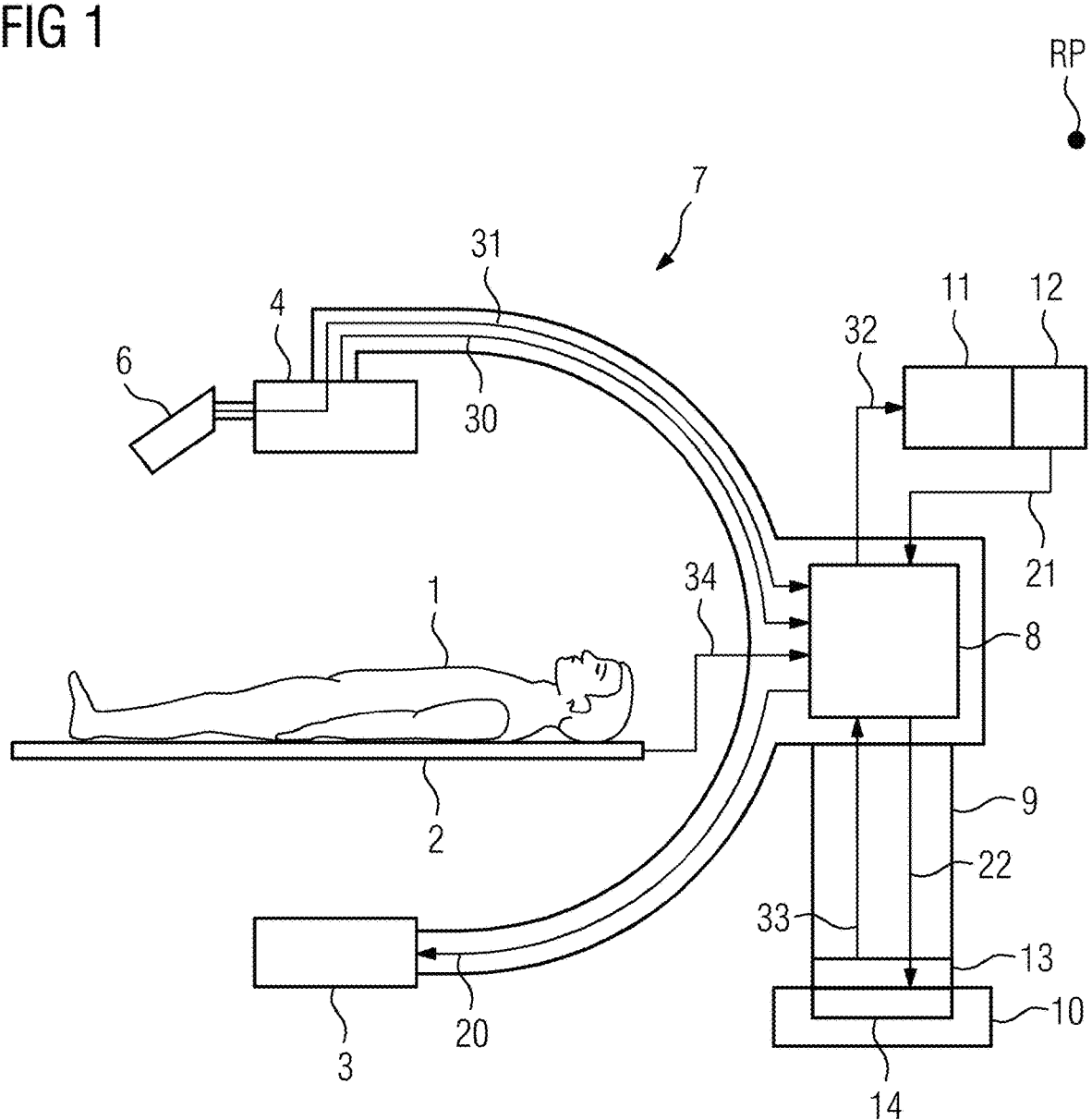
FIG. 1 is a schematic representation of one embodiment of a mobile medical X-ray device with a camera system.

In one embodiment, shown by way of example in FIG. 1, a medical X-ray device 7 includes an X-ray unit 3, a detector 4, a camera system 6, a movement apparatus 9, a sensor unit 13, a motorized drive 14, a mounting 10, a processing unit 8 (e.g., a processor), a display unit 11 (e.g., a display), and an input unit 12 (e.g., an input). For example, the X-ray device 7 may include a C-arm X-ray device.

To record an X-ray image of an examination subject 1, who is, for example, arranged on a patient-positioning unit 2, the processor 8 may send a control command 20 to the X-ray unit 3. The X-ray unit 3 transmits a beam of X-rays that, after illuminating the examination subject 1, impinges on a surface of the detector 4. The detector 4 may, for example, send a signal 30 to the processor 8, which acquires X-ray image information using the signal 30. The camera system 6 also has a defined position relative to the detector 4. The camera system 6 may be arranged such that the camera system 6 may record a data set that maps at least one section 61 of a surface structure of the examination subject 1. For this purpose, the camera system 6 may send a signal 31 to the processor 8, which, using the signal 31, may generate the data set that maps at least one section 61 of the surface structure of the examination subject 1.

For example, a graphic representation of a, for example, currently recorded section 61 of the surface structure of the examination subject 1 may be displayed on the display unit 11 (e.g., on a monitor and/or display).

The movement apparatus 9 of the X-ray device 7 also includes a sensor unit 13 (e.g., at least one optical sensor and/or mechanical sensor and/or electronic sensor) and a motorized drive 35. For example, the X-ray device 7 is embodied to acquire, at a first point in time, original positioning information. The X-ray device 7 is located in an original position UP at the first point in time 71. To determine the original positioning information, a sensor unit 13 that is arranged, for example, on and/or inside the movement apparatus 9 may, for example, send a signal 33 to the processor 8. For example, the movement apparatus 9 of the X-ray device 7 may include at least one wheel (not shown). The original positioning information pertaining to the X-ray device 7 may be at least partly acquired via wheel setting changes.

The sensor unit 13 may determine the alignment of the X-ray device 7 with respect to the examination subject 1 and/or to the patient-positioning device 2 and/or spatial positioning information. The sensor unit 13 may be embodied to map a pose of the X-ray device 7, for example, in the case of a robotic arm. For example, the original positioning information in the X-ray device 7 may be mapped via changes inside the movement apparatus 9 and/or relative to a mounting 10 of the movement apparatus 9 (e.g., by the sensor unit 13). For example, a graphic representation of the original positioning information may be displayed on the display unit 11.

Patient-positioning information may be assigned to the original positioning information, with a signal 34 being, for example, sent by the patient-positioning device 2 to the processor 8. In one embodiment, the original positioning information in the X-ray device may include the original position UP of the X-ray device in the room and/or relative to a point of reference RP (e.g., an intermediate position PP) in the room.

The display unit 11 may be configured to display at least one X-ray image and/or further information about, for example, recording parameters for an X-ray examination.

The input unit 12 may be embodied to facilitate the control of the movement of the X-ray device 7, for example, by an operator. For this purpose, the input unit 12 sends a control command 21 to the processor 8, which transmits, for example, a control command 22 to the motorized drive of the movement apparatus 9. This may allow a semi-automatic or automatic movement of the X-ray device 7. The specifying of the target position ZP may ensue through an input from an operator on the input unit 12. For this purpose, for example, a direction and a distance (e.g., a vector) relative to the original position UP may be specified.

The input unit 12 may allow the determination of recording parameters for an X-ray examination by an operator. For example, the display unit 11 may include a capacitive display and/or a touch-sensitive display. The input unit 12 may be incorporated into the display unit 11.

Figure 2:
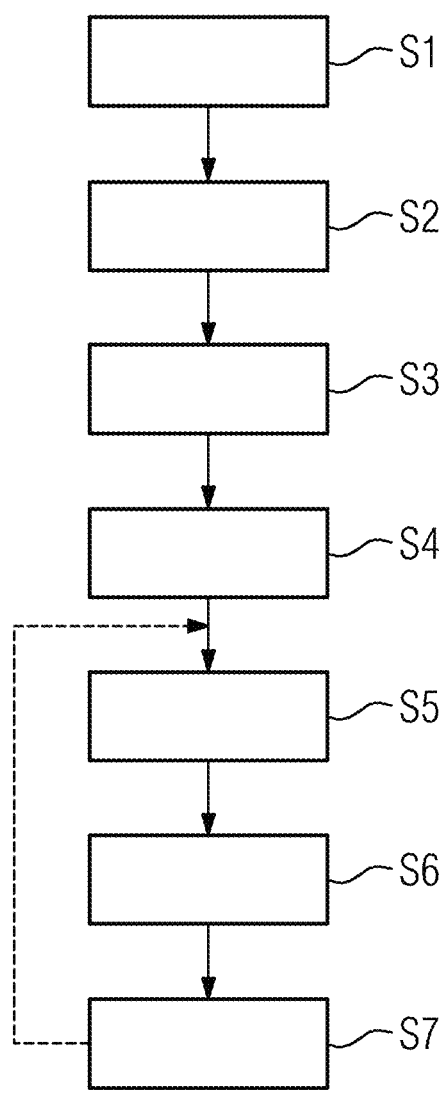
FIG. 2 is a schematic representation of one embodiment of process acts for increasing the accuracy of positioning of a mobile medical X-ray device relative to an examination subject using a camera system.

FIG. 2 shows a schematic view of the process acts for increasing the accuracy of positioning of a mobile medical X-ray device 7 relative to an examination subject 1 using a camera system 6. In a first act S1, a recording of a first data set, which maps at least one first section of the surface structure of the examination subject 61, may ensue at a first point in time using the camera system 6. In a second act S2, which, for example, may also ensue during the first act S1, original positioning information for the X-ray device 7 is acquired at the first point in time. The X-ray device 7 is located in an original position UP at the first point in time. Next, in a third act S3, a target position of the X-ray device relative to the original position is specified using the original positioning information and the first data set. In act S4, the X-ray device 7 is positioned 39 after the first point in time out of the original position UP and into a first approach position AP1 using the original positioning information. In a fifth act S5, a further data set that maps at least one further section of the surface structure of the examination subject 1 is recorded at a further point in time by the camera system 6. At the further point in time, the X-ray device 7 is located in the first approach position AP1. The at least one first section 61 and the at least one further section at least partly map a common region of the surface structure of the examination subject 1. In a sixth act S6, which may ensue during, for example, the fifth act S5, a deviation between the target position ZP and the first approach position AP1 is determined through a reconciliation between the first data set and the further data set. This may ensue, for example, using the processor 8. In a seventh act S7, the X-ray device 7 is positioned 42 out of the first approach position AP1 into a second approach position AP2 using the deviation that has been determined.

For example, the X-ray device 7 may be moved between the third act S3 and the fourth act S4 into an intermediate position PP (e.g., a parking position). The original position UP may be specified as an approach position ZP. The positioning 41 of the X-ray device 7 out of the intermediate position PP into the first approach position AP1 may also include, for example, the movement of the X-ray device back into an alignment and/or pose of the X-ray device 7 contained in the original positioning information.

For example, at a point in time during the positioning 42 of the X-ray device 7 out of the first approach position AP1 into the second approach position AP2, a correction of this positioning 42 of the X-ray device 7 may ensue. The correction includes recording of at least one further current data set and reconciliation of this further current data set with at least one data set recorded earlier. This may occur, for example, by repeating acts S5 to S7.

For example, in act S5, a deviation between the first data set and the further data set may be determined. A representation of the deviation, such as a representation in color and/or a numerical value, is displayed on the display unit 11.

The positioning 42 of the X-ray device 7 out of the first approach position AP1 into the second approach position AP2 may ensue semi-automatically or automatically. Using the deviation between the target position ZP and the first approach position AP1 determined in act S5, the processor 8 may provide, for example, a collision-free navigation of the movement of the X-ray device 7, advantageously considering further features in the surroundings of the X-ray device 7. With semi-automatic positioning 42, it is possible, for example, for an automatic alignment of a movement direction of the X-ray device 7 to ensue (e.g., by a control signal 22 that is sent by the processor 8 to the motorized drive 10). Feedback on the current alignment of the movement direction of the X-ray device may be provided via a signal 33 that is sent by the sensor unit 13 to the processor 8. A control of a speed of the movement of the X-ray device 7 may be provided through an input by an operator (e.g., via the input unit 12).

A parameter for a registrability between the, for example, last recorded further data set and the first data set, for example, may be determined by the processor 8. The parameter may be displayed on the display unit 11.

In a further embodiment, texture-related information may be assigned to each data set recorded. The texture-related information may be captured, for example, by the camera system 6 and/or via a further sensor (not shown), which is configured to send a signal to the processor 8.

Figure 3:
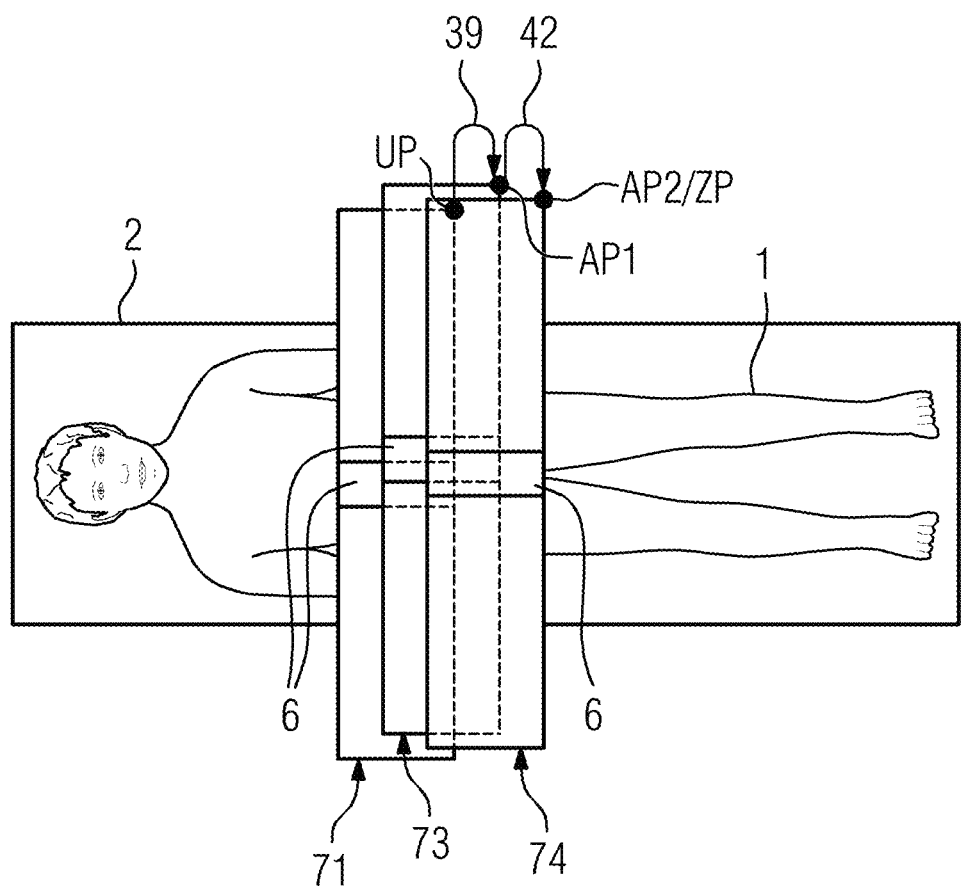
FIG. 3 is a schematic representation of the positioning of the X-ray device according to an embodiment of the proposed method.

FIG. 3 shows a schematic representation of the positioning of the X-ray device according to the proposed method. The examination subject 1 is arranged on a patient-positioning device 2. At the first point in time, the X-ray device 71 is located in the original position UP. At the first point in time according to act S1, a first data set that maps at least one first section of the surface structure 61 of the examination subject 1 is recorded by the camera system 6. After positioning of the X-ray device 7 has ensued after the first point in time out of the original position UP into a first approach position AP1, according to act S4, by a movement 39, the X-ray device 73 is located in the first approach position AP1.

According to act S5, a further data set, which maps at least one further section of the surface structure of the examination subject, is recorded at a further time by the camera system 6. The X-ray device 73 is located in the first approach position AP1 at the further point in time, and the at least one further section at least partly maps a common region of the surface structure of the examination subject 1. After a deviation between the target position ZP and the first approach position AP1 has been determined according to act S6, the X-ray device 73 is positioned 42 out of the first approach position AP1 into a second approach position AP2 by the deviation that has been determined. Ideally, the second approach position AP2 coincides with the specified target position ZP.

Figure 4:
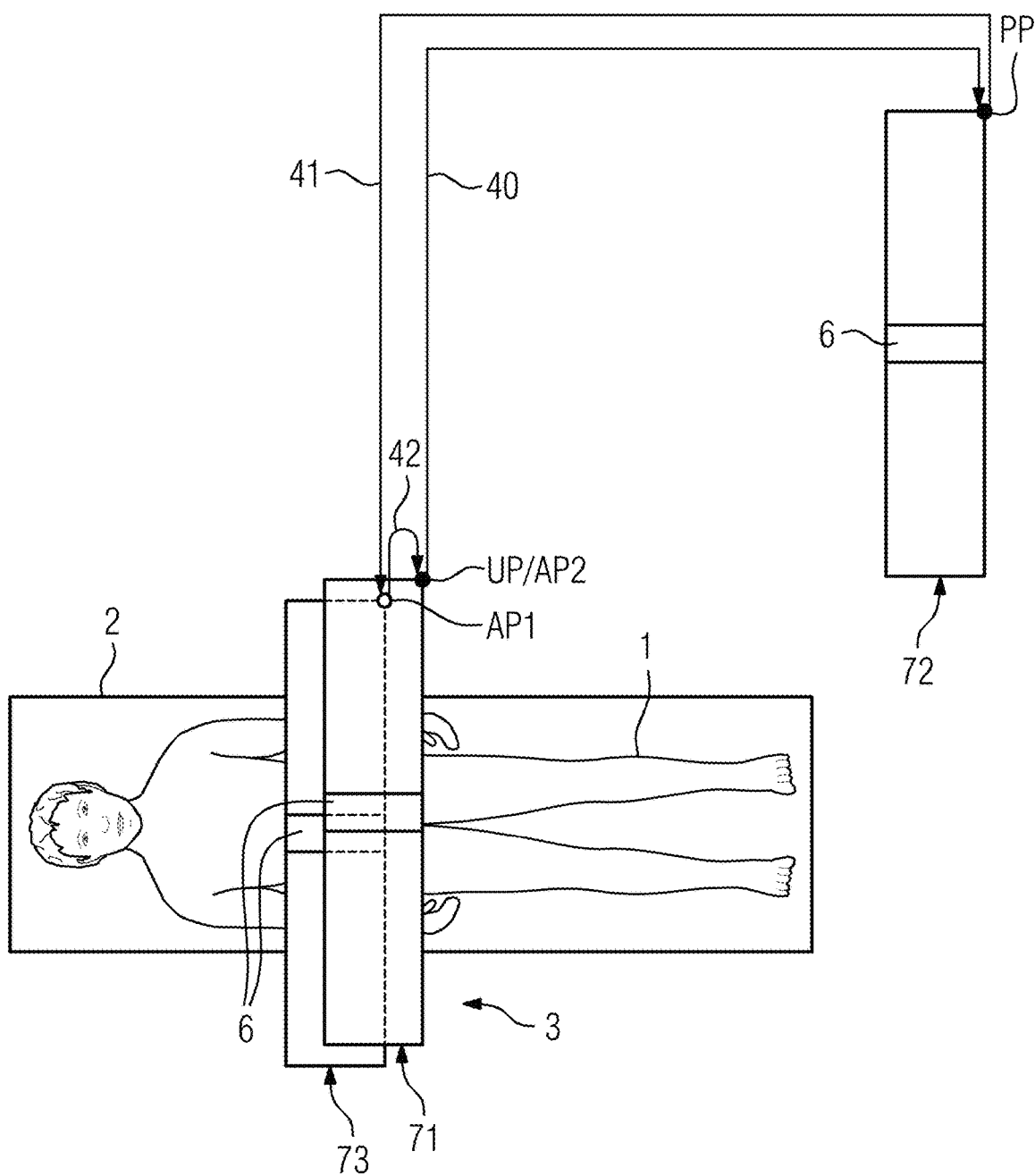
FIG. 4 is a schematic representation of the positioning of the X-ray device according to another embodiment, where the X-ray device is moved into an intermediate position.

FIG. 4 shows a schematic representation of the positioning of the X-ray device 7, where the X-ray device 7 is moved into an intermediate position PP. The examination subject 1 is arranged on a patient-positioning device 2. At the first point in time, the X-ray device 71 is located in the original position UP, where at the first point in time according to act S1, a first data set, which maps at least one first section of the surface structure 61 of the examination subject 1, is recorded by the camera system 6. According to one variant of act S3, the original position UP is specified as the target position ZP.

After a change in the position of the X-ray device 7 after the first point in time, out of the original position UP, and into an intermediate position PP by a movement 40, the X-ray device 72 is located in the intermediate position PP. Next, the X-ray device is positioned 41 out of the intermediate position into the first approach position AP1. According to act S5, a further data set, which maps at least one further section of the surface structure of the examination subject, is recorded at a further point in time by the camera system 6. The X-ray device 73 is located in the first approach position AP1 at the further point in time, and the at least one further section at least partly maps a common region of the surface structure of the examination subject 1. After a deviation between the target position ZP, which is specified as, for example, the original position UP, and the first approach position AP1 has been determined according to act S6, the X-ray device 73 is positioned 42 out of the first approach position AP1 into a second approach position AP2 using the deviation that has been determined. The second approach position AP2 may coincide with the original position UP.

Figure 5:
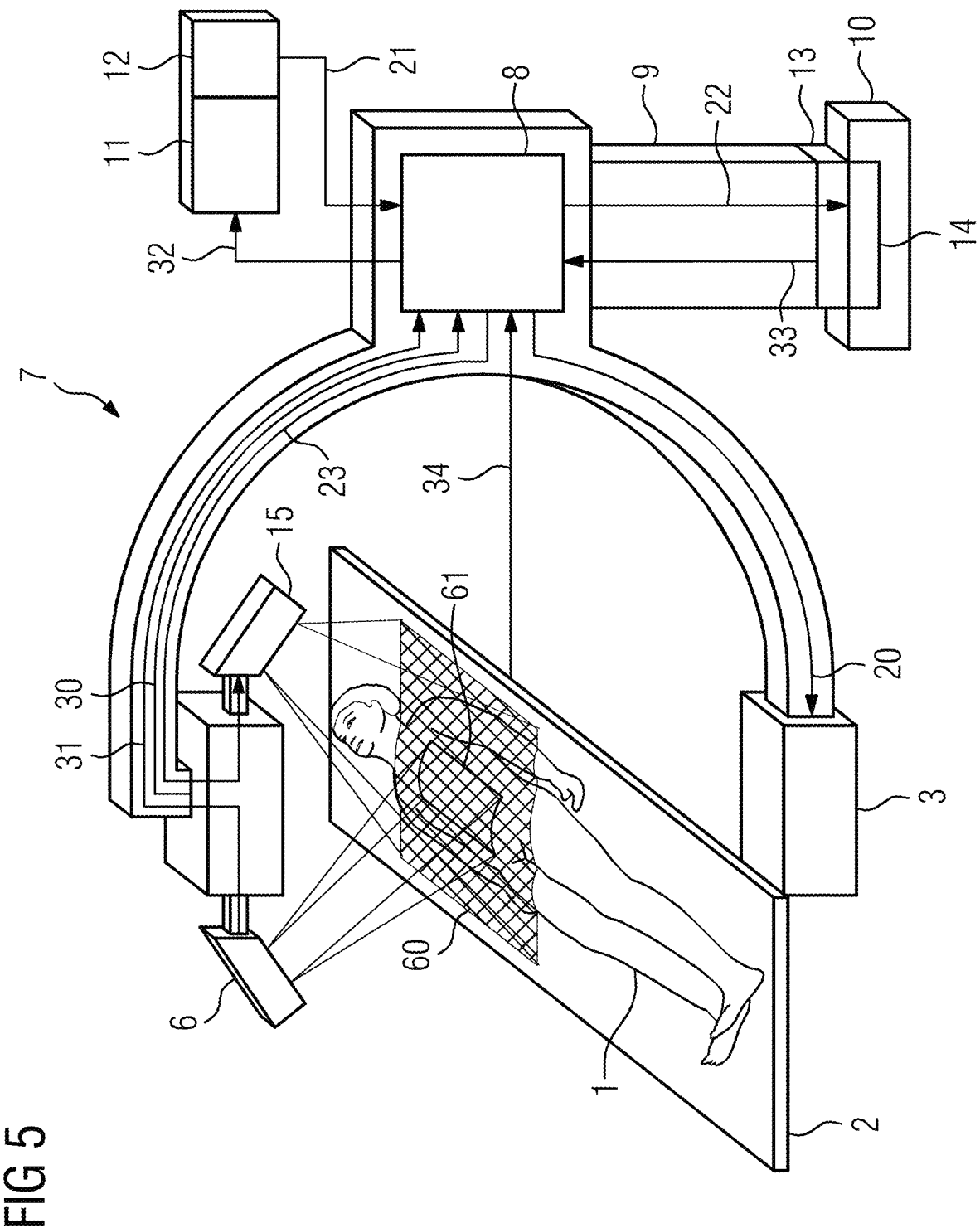
FIG. 5 is a schematic representation of one embodiment of a mobile medical X-ray device with a camera system and projection equipment.

In the embodiment shown in FIG. 5, the X-ray device 7 includes projection apparatus 15 that is configured to project a graphic pattern 60 onto the surface 60 of the examination subject 1 that may be captured by a camera system 6. For example, a control command 23 may be sent for this purpose by the processor 8 to the projection apparatus 15. Using the control command 23, the graphic pattern 60 and/or a projection characteristic, such as, for example, a light setting and/or an alignment of the projection apparatus 15, may be set. For this purpose, an input by an operator (e.g., a signal 21) may be processed by the processor 8 via the input unit 12 and converted into a control command 23 for the projection apparatus 15. By the projection of a graphic pattern 60 onto the surface 61 of the examination subject 1 that may be detected by a camera system 6, mapping of the surface structure of the examination subject by a single camera may be facilitated.

Figure 6:
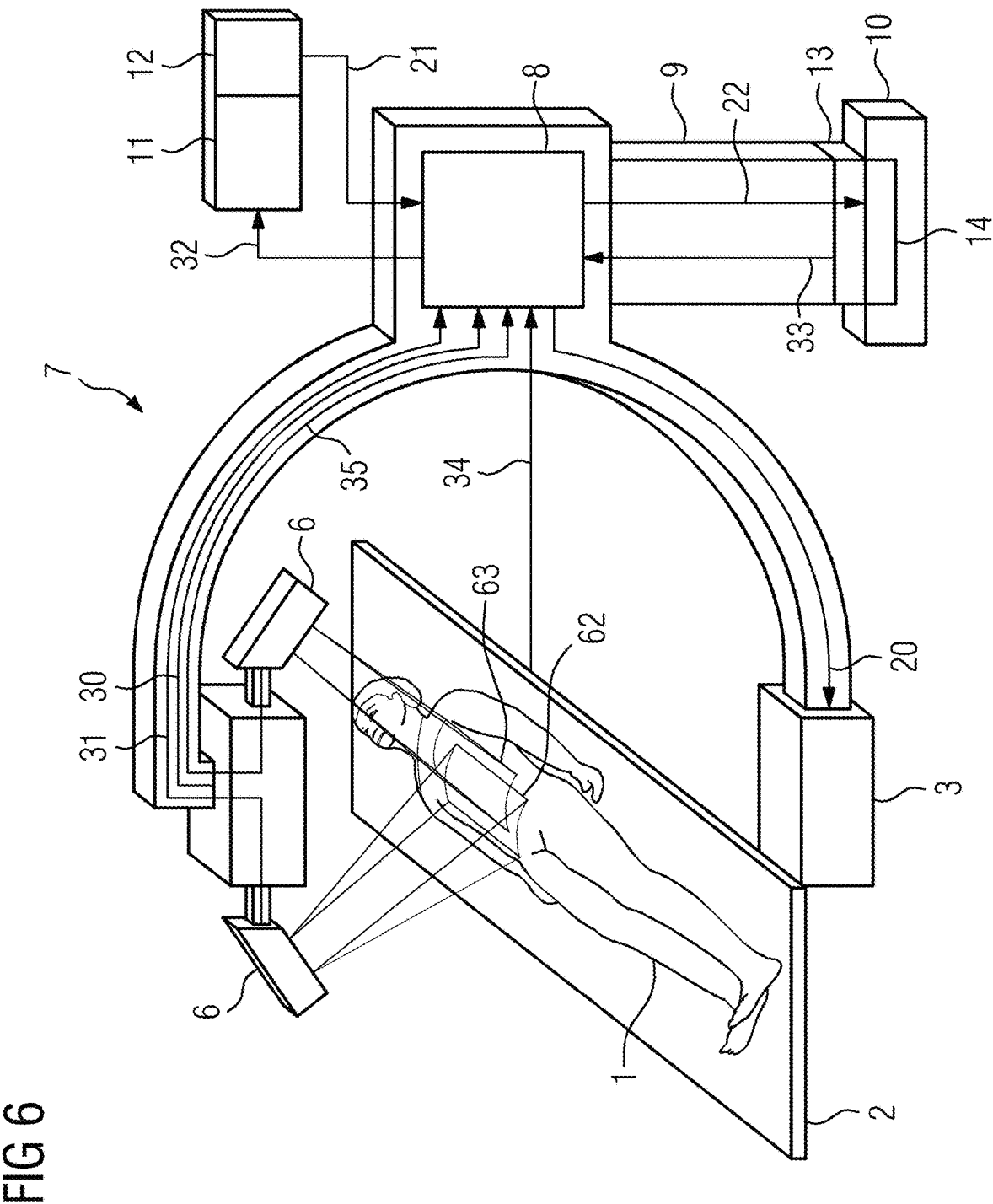
FIG. 6 is a schematic representation of one embodiment of a mobile medical X-ray device with a camera system to generate stereoscopic information.

FIG. 6 shows a further embodiment of the proposed method, where the camera system 6 includes at least two cameras. The at least two cameras each record at least one data subset 62 and 63, respectively. The data subsets 62 and 63 each map at least one common section of the surface of the examination subject 1. The data subsets include stereoscopic information. The stereoscopic information maps at least one section of the surface structure of the examination subject 1 (e.g., the common section of the surface of the examination subject 1) that is mapped in the data subsets. For example, the stereoscopic information may be acquired by the camera system 6 in the processor 8 using the signals 31 and 35. The first data set and the further data set each include at least one data subset for each of the at least two cameras. For example, the at least two cameras in the camera system 6 may be embodied to include in each case light sensitive regions and/or image resolution regions and/or focal lengths. As a result, better mapping of the surface structure of the examination subject 1 may be achieved by combining the data subsets in the processor 8. For example, the camera system 6 with the at least two cameras may include further recording units that are embodied to map further subregions and/or further properties of the surface of the examination subject 1. For example, via an input by an operator using the input unit, control of the alignment of the at least two cameras in the camera system and/or of a recording setting of the individual cameras may be facilitated. Further, a graphic representation of, for example, the current, stereoscopic information that has been acquired and/or of the individual data subsets may be provided on the display unit 11.

The detailed methods described in the aforementioned and the X-ray device shown are merely embodiments that may be modified in a great variety of ways by a person skilled in the art without departing from the scope of the invention. The use of the indefinite article "a" or "an" does not preclude the relevant features from being present in plurality. Likewise, the term "unit" does not preclude the relevant components from consisting of a plurality of interacting components that may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for increasing accuracy of positioning of a mobile medical X-ray device relative to an examination subject by a camera system, the method comprising:
   recording a first data set that maps at least one first section of a surface structure of the examination subject at a first point in time by the camera system, wherein the mobile medical X-ray device comprises a detector, and wherein the camera system has a defined position relative to the detector;
   acquiring original positioning information pertaining to the mobile medical X-ray device at the first point in time, wherein the mobile medical X-ray device is located in an original position at the first point in time;
   specifying a target position of the mobile medical X-ray device relative to the original position, wherein the original position is described by the original positioning information and the first data set;
   positioning the mobile medical X-ray device after the first point in time out of the original position into a first approach position using the original positioning information;
   recording a second data set that maps at least one second section of the surface structure of the examination subject at a second point in time by the camera system, wherein the X-ray device is located at the second point in time in the first approach position, and wherein the at least one first section and the at least one second section at least partly map a common region of the surface structure of the examination subject;
   determining a deviation between the target position and the first approach position through a reconciliation between the first data set and the second data set; and
   positioning the X-ray device out of the first approach position into a second approach position using the determined deviation.

2. The method of claim 1, further comprising moving the X-ray device to an intermediate position before positioning into the first approach position.

3. The method of claim 2, wherein the original position is specified as the target position.

4. The method of claim 1, further comprising displaying a graphic representation of a recorded section of the surface structure of the examination subject on a display unit.

5. The method of claim 1, further comprising:
   determining a deviation between the first data set and the second data set; and
   displaying a representation of the deviation on a display unit.

6. The method of claim 1, wherein, at a point in time during the positioning of the X-ray device out of the first approach position into the second approach position, a correction of the positioning of the X-ray device ensues, and
   wherein this correction includes a recording of at least one further current data set and a reconciliation of the at least one further current data set with at least one data set recorded earlier.

7. The method of claim 1, wherein the positioning of the X-ray device out of the first approach position into the second approach position ensues semi-automatically or automatically.

8. The method of claim 1, further comprising:
    determining a parameter for a registrability between a last recorded second data set and the first data set; and
    displaying the parameter on a display unit.

9. The method of claim 1, further comprising projecting a graphic pattern onto the surface of the examination subject, the projected graphic pattern being detectable by the camera system.

10. The method of claim 1, wherein the camera system includes at least two cameras,
    wherein each of the at least two cameras records at least one data subset that maps at least one common section of a surface of the examination subject,
    wherein the data subsets include stereoscopic information,
    wherein the stereoscopic information maps at least one section of the surface structure of the examination subject, and
    wherein the first data set and the second data set each include at least one data subset for each of the at least two cameras.

11. The method of claim 1, wherein patient-positioning information is assigned to the original positioning information, and
    wherein the registration of the first data set onto a change in the patient-positioning information ensues at the time of recording the second data set.

12. The method of claim 1, wherein texture-related information is assigned to each recorded data set.

13. The method of claim 1, wherein the mobile X-ray device comprises a movement apparatus, and
    wherein the original positioning information pertaining to the X-ray device is acquired via changes inside the movement apparatus, relative to a mounting of the movement apparatus, or a combination thereof.

14. The method of claim 13, wherein the movement apparatus comprises at least one wheel, and
    wherein the original positioning information pertaining to the X-ray device is acquired at least partly via setting changes of the at least one wheel.

15. A medical X-ray device comprising:
    a detector;
    a camera system configured to record a first data set that maps at least one first section of a surface structure of the examination subject at a first point in time, wherein the camera system has a defined position relative to the detector, wherein the camera system is further configured to acquire original positioning information pertaining to the medical X-ray device at the first point in time, wherein the detector is located in an original position at the first point in time, wherein the camera system is further configured to specify a target position of the medical X-ray device relative to the original position, the original position being described by the original positioning information and the first data set, wherein the detector is positionable after the first point in time out of the original position into a first approach position using the original positioning information, and wherein the camera system is further configured to record a second data set that maps at least one second section of the surface structure of the examination subject at a second point in time, the detector being located at the second point in time in the first approach position, and the at least one first section and the at least one second section at least partly mapping a common region of the surface structure of the examination subject; and
    a processor configured to determine a deviation between the target position and the first approach position through a reconciliation between the first data set and the second data set,
    wherein the detector is positionable out of the first approach position into a second approach position using the determined deviation.

16. The medical X-ray device of claim 15, further comprising a display unit.

17. The medical X-ray device of claim 15, further comprising a projection apparatus that is configured to project a graphic pattern onto the surface of the examination subject, the projected graphic pattern being detectable by the camera system.

18. The medical X-ray device of claim 15, wherein the camera system includes at least two cameras,
    wherein the at least two cameras are configured to record at least one data subset that maps at least one common section of a surface of the examination subject,
    wherein the at least one data subset includes stereoscopic information,
    wherein the stereoscopic information maps at least one section of the surface structure of the examination subject, and
    wherein the first data set and the second data set each include at least one data subset from each of the at least two cameras.

19. The medical X-ray device of claim 15, further comprising a movement apparatus,
    wherein the original positioning information pertaining to the X-ray device is acquirable via changes inside the movement apparatus, relative to a mounting of the movement apparatus, or a combination thereof.

20. The medical X-ray device of claim 15, further comprising a movement apparatus that includes at least one wheel,
    wherein the original positioning information pertaining to the medical X-ray device is at least partly acquirable via setting changes of the at least one wheel.

21. In a non-transitory computer-readable storage medium that stores instructions executable by one or more processors to increase accuracy of positioning of a mobile medical X-ray device relative to an examination subject by a camera system, the instructions comprising:
    recording a first data set that maps at least one first section of a surface structure of the examination subject at a first point in time by the camera system, wherein the mobile medical X-ray device comprises a detector, and wherein the camera system has a defined position relative to the detector;
    acquiring original positioning information pertaining to the mobile medical X-ray device at the first point in time, wherein the mobile medical X-ray device is located in an original position at the first point in time;
    specifying a target position of the mobile medical X-ray device relative to the original position, wherein the original position is described by the original positioning information and the first data set;
    positioning the mobile medical X-ray device after the first point in time out of the original position into a first approach position using the original positioning information;
    recording a second data set that maps at least one second section of the surface structure of the examination subject at a second point in time by the camera system, wherein the X-ray device is located at the second point in time in the first approach position, and wherein the at least one first section and the at least one second section at least partly map a common region of the surface structure of the examination subject;

determining a deviation between the target position and the first approach position through a reconciliation between the first data set and the second data set; and positioning the X-ray device out of the first approach position into a second approach position using the determined deviation.

* * * * *